United States Patent [19]
Keller, Jr. et al.

[11] Patent Number: 4,513,084
[45] Date of Patent: Apr. 23, 1985

[54] **MUTANT STRAIN OF *CLOSTRIDIUM THERMOACETICUM* USEFUL FOR THE PREPARATION OF ACETIC ACID**

[75] Inventors: Frederick A. Keller, Jr., Naperville; Jeffrey S. Ganoung, Brookfield; Susan J. Luenser, LaGrange Park, all of Ill.

[73] Assignee: CPC International Inc., Englewood Cliffs, N.J.

[21] Appl. No.: 474,608

[22] Filed: Mar. 11, 1983

[51] Int. Cl.$^3$ .......................... C12P 7/54; C12N 15/00; C12N 1/20; C12J 1/00
[52] U.S. Cl. ................................. 435/140; 435/172.1; 435/253; 435/813; 435/842; 426/17
[58] Field of Search ...................... 435/140, 172.1, 253, 435/289, 290, 801, 813, 842; 426/17

[56] References Cited

U.S. PATENT DOCUMENTS

| | | | |
|---|---|---|---|
| 4,282,323 | 8/1981 | Yates | 435/140 |
| 4,371,619 | 2/1983 | Schwartz et al. | 435/842 |
| 4,405,717 | 9/1983 | Urbas | 435/842 |
| 4,425,432 | 1/1984 | Zeikus | 435/140 |

FOREIGN PATENT DOCUMENTS 572762  10/1945  United Kingdom ................ 435/140

OTHER PUBLICATIONS

Fontaine, et al., *J. Bacteriol.*, 43, 701–715 (1942).
Wang, et al., AIChE Symp. Ser. 181, 74, 105–110 (1978).
Schwartz, et al., *Applied and Environmental Microbiology*, 43, 117–123 and 1385–1392 (1982).

*Primary Examiner*—Alvin E. Tanenholtz
*Assistant Examiner*—Dinah H. Lewitan
*Attorney, Agent, or Firm*—Stanley M. Parmerter

[57] ABSTRACT

A biologically pure mutant of *C. thermoaceticum* (ATCC No. 39,289) useful for the production of acetic acid by a fermentation reaction. This mutant is capable of growing at a pH below 5.0 and shows a specific growth rate of at least 0.30 hr$^{-1}$ when continuously cultured under optimum conditions.

9 Claims, No Drawings

MUTANT STRAIN OF *CLOSTRIDIUM THERMOACETICUM* USEFUL FOR THE PREPARATION OF ACETIC ACID

FIELD OF THE INVENTION

This invention relates to a novel mutant strain of *Clostridium thermoaceticum* and to its use in the preparation of acetic acid.

BACKGROUND OF THE INVENTION

The production of organic chemicals by microorganisms is well known to those familiar with the fermentation art. Such fermentation reactions frequently produce a variety of products in dilute aqueous solutions. The expense of separating the chemicals from each other and from the large volumes of water has been so great that production of chemicals by fermentation has not been able to compete with the production of the same chemicals from fossil fuel sources. However, the gradual depletion of petroleum fossil fuel with a resultant increase in prices of petrochemical feedstocks has revived interest in fermentation reactions which can convert renewable raw materials into simple organic chemicals.

Fermentations that produce a single product are particularly desirable since product isolation from such reactions is simplified. Certain microorganisms, known as homoacidogens, can be used in such a procedure to give a single acid when grown on a variety of hexoses, pentoses and lactic acid. The fermentation of a hexose such as glucose by *Clostridium thermoaceticum*, hereafter abbreviated *C. thermoaceticum*. is especially attractive since it can produce theoretically 3 moles of acetic acid from 1 mole of the sugar.

*C. thermoaceticum* was first isolated by Fontaine, et al, *J. Bacteriol.*, 43, 701–715 (1942). The wild strain is an anaerobe that grows best at a pH of about 7. Its growth is inhibited by low pH, acetic acid, and acetate. For these reasons, this strain does not produce acetic acid in high concentration.

Various workers have attempted to obtain mutant strains of *C. thermoaceticum* that would produce higher concentrations of acetic acid in a fermentation reaction. Wang, et al, AIChE Symp. Ser. 181, 74, 105–110 (1978), described an improved strain of the microorganism that had a higher tolerance for sodium acetate. Schwartz and Keller, *Applied and Environmental Microbiology*, 43, 117–123 (1982), reported isolation of a strain of *C. thermoaceticum* capable of growing and producing acetic acid at a pH of 4.5. This work is also disclosed in European patent application No. 81104811.5, published June 1, 1982.

We have now isolated a new mutant of *C. thermoaceticum*, capable of growing at a pH of less than 5, which is a more efficient producer of acetic acid than any of the strains previously reported.

SUMMARY OF THE INVENTION

In accordance with the present invention, there is provided a biologically pure culture of a mutant strain of the microorganism *C. thermoaceticum*, ATCC No. 39,289, useful for the production of acetic acid when grown in an aqueous medium containing assimilable sources of carbon, nitrogen and inorganic substances. This culture is capable of growing at a pH below 5.0 at a temperature of from 50° C. to 65° C. It also has a specific growth rate of at least about 0.30 hr$^{-1}$ when grown in a continuous culture at pH 7 and 58° C.

Also provided in accordance with this invention is a method for converting carbohydrates to acetic acid by growing *C. thermoaceticum* in an anaerobic fermentor on an aqueous medium containing assimilable sources of carbon, nitrogen and inorganic substances, wherein the improvement comprises using a biologically pure culture of the mutant strain of *C. thermoaceticum*, ATCC No. 39,289, in a pH controlled continuous fermentation at a pH of about 5 to about 8, at a temperature of about 50° C. to about 65° C. and at a dilution rate of about 0.01 to about 0.40 per hour.

DETAILED DESCRIPTION OF THE INVENTION

The parent culture used for the development of the mutant strain of this invention was a wild type of *C. thermoaceticum*, DSM 521. The cultures used were obtained from the Massachusetts Institute of Technology, whose workers in turn had obtained it from Dr. H. G. Wood, Case Western Reserve University, Cleveland, Ohio.

Growth was monitored by measuring the absorbance at 540 nm. A Spectronic 20 spectrophotometer (Bausch & Lomb, Inc., Rochester, N.Y.) was used for the measurements. The sample was diluted with distilled water to read between 0.1 and 0.7 absorbance and the measurements were made in matched Hungate tubes of 16 mm outside diameter against a distilled water blank. Two or three grains of sodium dithionite were added to the diluted sample prior to reading when resazurin indicator was used to maintain it in its colorless state.

Acetic acid and glucose concentrations were determined using high-performance liquid chromatography (HPLC). A sample of fermentation mixture was centrifuged at about 10,000×g for 10 minutes to pellet the cells. Components of the supernatant were chromatographed by elution with 0.06 N $H_2SO_4$ from a cation-exchange resin in the hydrogen form. The eluted components were detected by means of a differential refractometer, plotted on a recorder and quantitated using an electronic integrator. The area underneath the curve which represents concentration of each component was reported as a percentage of the total area. The general procedure is that given in "Analyses of Carbohydrate Mixtures by Liquid Chromatography", *Am. Soc. Brew. Chem. Proc.*, 1973, pp.43–46. The separations were made on a 1-foot HPX-87 column in the hydrogen form, available from Bio-Rad Laboratories, Richmond, Calif.

In the description of this invention, the words "dilution rate", as used in this application, have the dimensions of per hour (hr$^{-1}$). This rate is obtained by dividing the flow rate of the medium in volume units per hour by the operating volume of the reactor.

The term "specific growth rate", as used herein, represents the rate of growth per unit amount of biomass in the fermentation reactor. It also has the dimension of reciprocal time (hr$^{-1}$). When a continuous fermentation vessel is operating at steady state conditions, the amount of biomass in the culture is constant and the specific growth rate equals the dilution rate.

The maximum specific growth rate was determined by the method described in Pirt, S. J., "Principles of Microbe and Cell Cultivation", John Wiley & Sons, New York, 1975, p. 33. This was accomplished by increasing the flow rate in the chemostat above the rate at which washout of the cells occurs. Absorbance readings were measured at various times and the natural logarithms of the optical density readings were plotted against time. The slope of this line plus the dilution rate at which washout occurred represents the maximum specific growth rate for the microorganism. The mass doubling time for the cells, also called the generation time, is calculated by dividing ln 2 by the maximum specific growth rate.

The parent organism was grown in a chemostat using conditions of continuous culture in a medium in which the pH was gradually lowered over a period of time. The operation of such a chemostat and its use for obtaining spontaneous mutations of bacteria growing in it was described by Novick, A. and Szillard, L., *Science*, 112, 715–716 (1950). The chemostat operation used the principle of biomass feedback in which the amount of nutrient fed to the growing culture was controlled by the pH of the medium. This technique is designed to select for genetically different organisms, in this case those growing more rapidly at lower pH. Using this technique, a mutant strain was obtained which would grow in a medium having a pH of 5.0 or below. This mutant strain is distinctly different from the parent strain of *C. thermoaceticum*, which shows little growth in a medium with a pH below about 6.4.

The mutant strain of the microorganism described herein is a new composition of matter. It has been deposited in the American Type Culture Collection in Rockville, Md., and will be maintained in that depository during the life time of this patent. It is available as ATCC No. 39,289.

The mutant strain of this invention is a thermophilic anaerobe that is grown in a medium and under an atmosphere from which oxygen has been excluded. It is capable of growing in an aqueous medium containing assimilable sources of carbon, nitrogen and inorganic substances at a pH below 5.0 to produce acetic acid. Preferred carbon sources are glucose and fructose. Although growth and acetic acid production occur slowly at a pH below 5.0, they occur more rapidly at higher pH with a preferred pH being between about 6:9 and 7.4. Growth of the microorganism occurs at a temperature from about 50° C. to about 65° C. with a preferred temperature being in the range of about 56° C. to about 60° C. The mutant strain is capable of growing with a specific growth rate of at least about 0.30 $hr^{-1}$ at pH 7 and 58° C.

The mutant strain of this invention is useful for converting carbohydrates to acetic acid when it is grown in an anaerobic fermentor in a pH controlled continuous fermentation. Such a fermentation can be carried out at a dilution rate of from 0.01 to 0.4 per hour when the pH is controlled in a range of from 5 to 8 and the temperature is held in the range of from 50° C. to 65° C.

The present mutant strain differs from the parent in its ability to grow in a medium at pH 5. In addition, it shows a maximum specific growth rate about 50% greater than that of the parent strain when both are grown in a medium at pH 7.

The mutant strain and process of this invention are futher illustrated by the following examples:

EXAMPLE 1

The parent strain of the microorganism, *C. thermoaceticum* (DSM 521), was kindly furnished to us by workers at the Massachusetts Institute of Technology, who in turn had obtained it from Dr. H. G. Wood, Case Western Reserve University, Cleveland, Ohio. It is available from the Deutsche Sammlung von Mikroorganismen in Göttingen, West Germany, as DSM 521.

Medium preparation and cultivation of samples were carried out using standard anaerobic techniques as described by Hungate, R. E., "A Roll Tube Method for Cultivation of Strict Anaerobes", in *Methods in Microbiology*, edited by J. R. Norris and D. W. Ribbons, Vol. 3B, Academic Press, New York, 1969, pp. 117–132, and by Miller and Wolin, *Appl. Microbiol.*, 27, 985 (1974).

The medium used for growth of the organism had the following composition:

| GROWTH MEDIUM | |
|---|---|
| Component | Concentration (g/liter) |
| A. Glucose | 30.0 |
| B. $NaHCO_3$ | 16.8 |
| $K_2HPO$ | 7.0 |
| $KH_2PO_4$ | 5.5 |
| C. Yeast Extract | 5.0 |
| Tryptone | 5.0 |
| $(NH_4)_2SO_4$ | 1.0 |
| $MgSO_4.7H_2O$ | 0.25 |
| $Fe(NH_4)_2(SO_4)_2.6H_2O$ | 0.04 |
| $Co(NO_3)_2.6H_2O$ | 0.03 |
| $NaMoO_4.2H_2O$ | 0.0024 |
| Resazurin (0.20 g/100 ml solution) | 1.0 ml/l |

Solutions of components of Groups A, B, and C were sterilized separately before combining to make a medium of the given composition. Then 0.5 g of sodium thioglycolate, 5.6 mg of nicotinic acid and 1 ml of a trace salt solution were added per liter of medium. The trace salt solution had the following composition:

| TRACE SALT SOLUTION | |
|---|---|
| Component | Concentration (g/liter) |
| Ethylenediaminetetraacetic Acid Disodium Salt Dihydrate | 5.00 |
| $MnCl_2.4H_2O$ | 5.00 |
| $Na_2SeO_3$ | 0.20 |
| $H_3BO_3$ | 0.100 |
| $ZnCl_2$ | 0.050 |
| $AlK(SO_4)_2.12H_2O$ | 0.100 |
| $NiCl_2.6H_2O$ | 0.020 |
| $CuCl_2.2H_2O$ | 0.010 |

A continuous fermentation was carried out in a 1-liter Bellco fermentor (Bellco Glass Inc., Vineland, N.J.). This fermentor was fitted with an inlet tube for medium addition, an overflow outlet tube, a magnetically driven agitator and an Ingold pH probe (Ingold Electrodes Inc., Andover, Mass.). The pH probe was attached to a Chemtrix type 45 AR pH controller (Chemtrix Inc., Hillsboro, Oreg.). The pH controller activated peristaltic pumps which added medium and removed effluent from the fermentor whenever the pH reached a low-control set point. This arrangement required that the culture generate sufficient acetic acid to lower the pH to the control point before fresh medium was added to the fermentor to raise the pH back above the control point. The level of medium in the fermentor was kept constant by the overflow effluent pump system and the fermentor was constantly mixed and sparged with pure $CO_2$ at a slight positive pressure (2 to 3 cm $H_2O$). The temperature was maintained at 58°±1° C. by means of heated propylene glycol which circulated through the jacket of the fermentor.

The original culture was grown in a medium with the pH set at 6.3. As the organism grew, selection for faster-growing organisms occurred and the rate of medium delivery increased. Once a stable near-equilibrium condition was reached, the pH control point was lowered about 0.1 pH unit. Selection was then continued at this lower pH until a new equilibrium condition was reached. Following this procedure, it was possible to obtain a culture of *C. thermoaceticum* growing at or below a pH of 5.0. A discrete colony of this new mutant was isolated, replicated and grown in fresh medium. The cells were stored by freezing in glycerine or by lyophilization. This strain is available from the American Type Culture Collection as ATCC No. 39,289.

Although the strain grows at pH 5 or slightly below, the specific growth rate at this pH is quite small. The maximum observed specific growth rate at pH 5 was 0.023 $hr^{-1}$, corresponding to a generation time of 30 hours. The product concentration in a continuous reactor operated under these conditions averaged about 10 g/l. However, when this strain was grown in a chemostat at a neutral pH, a much improved growth rate was observed as noted in the following example.

EXAMPLE 2

The low pH tolerant strain of *C. thermoaceticum* isolated in Example 1 was grown in a chemostat held at a pH of 7.0 and at a temperature of 58°±1° C. The equipment and operation of the chemostat was similar to that given in Example 1 except that a constant delivery feed pump was used in place of the pH control pump for supplying medium to the fermentor. Fermentor volume was kept constant by use of an effluent tube positioned at the desired level. Steady state growth rates of from 0.25 $hr^{-1}$ to 0.31 $hr^{-1}$ were observed. The maximum specific growth rate was determined to be 0.33 $hr^{-1}$ which corresponds to a mass doubling time of 2.1 hours. This compares with a maximum specific growth rate of 0.22 $hr^{-1}$ for the parent culture as reported by Wang, et al, AIChE Symp. Ser. 181, 74, 105-110 (1978).

EXAMPLE 3

The low pH tolerant strain of *C. thermoaceticum* isolated in Example 1 was compared with the parent strain in these further experiments. Both strains were grown to log phase before 0.3-ml samples were used to inoculate 10 ml of growth medium in 18-mm, aluminum-sealed, Bellco tubes (Bellco Glass, Inc., Vineland, N.J.). The growth medium was of the same concentration as that used in Example 1 except that the concentration of glucose was 2% and the buffer salts (Group B of the medium) were only half as concentrated. The pH of the medium was adjusted with acetic acid. The tubes were incubated at 58° C. with $CO_2$ in the headspace. When the initial pH of the medium was 5.5, only the mutant strain of this invention showed growth as measured by increase in absorbance readings. After an initial lag period of about 40 hours, it grew at a specific growth rate of 0.063 $hr^{-1}$. In contrast, the parent strain showed no growth even after incubation for 120 hours.

When the initial pH of the medium was 6.1, the mutant strain of this invention exhibited a specific growth rate of 0.099 $hr^{-1}$ with almost no lag period. The parent strain, after an initial lag period of about 10 hours, grew at a specific growth rate of 0.069 $hr^{-1}$.

Thus, it is apparent that there has been provided, in accordance with the invention, a strain of *C. thermoaceticum* useful for the production of acetic acid which is superior to the strains of the prior art. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A biologically pure culture of a mutant strain of the microorganism *C. thermoaceticum*, ATCC No. 39,289, useful for the production of acetic acid when grown in an aqueous medium containing assimilable sources of carbon, nitrogen and inorganic substances, which grows at a pH below 5.0 at a temperature of from 50° C. to 65° C. and has a specific growth rate of at least about 0.30 $hr^{-1}$ when grown in a continuous culture at pH 7 and 58° C.

2. In a method for converting carbohydrates to acetic acid by growing *C. thermoaceticum* in an anaerobic fermentor on an aqueous medium containing assimilable sources of carbon, nitrogen and inorganic substances and separating the acetic acid from the medium, wherein the improvement comprises using a biologically pure culture of the mutant strain of *C. thermoaceticum*, ATCC No. 39,289, in a pH controlled continuous fermentation at a pH of about 5 to about 8, at a temperature of about 50° C. to about 65° C. and at a dilution rate of about 0.01 to about 0.40 per hour.

3. The method of claim 2 wherein the assimilable source of carbon is selected from the group consisting of glucose, fructose, and mixtures of glucose and fructose.

4. The method of claim 2 wherein the fermentation is carried out at a pH between about 6.9 and 7.4.

5. The method of claim 4 wherein the pH of the fermentation is controlled at a pH of about 7.

6. The method of claim 2 wherein the fermentation is carried out at a temperature between about 56° C. and about 60° C.

7. The method of claim 6 wherein the temperature is controlled at 58°±1° C.

8. The method of claim 7 wherein the pH of the fermentation is controlled at a pH of about 7.

9. The method of claim 8 wherein the assimilable source of carbon is selected from the group consisting of glucose, fructose and mixtures of glucose and fructose.

* * * * *